United States Patent
Lieberman

(10) Patent No.: US 8,690,900 B2
(45) Date of Patent: Apr. 8, 2014

(54) APPARATUS AND METHOD FOR CONNECTING TWO ELONGATE BODY TISSUES

(75) Inventor: Isador H. Lieberman, Plano, TX (US)

(73) Assignee: The Cleveland Clinic Foundation, Cleveland, OH (US)

( * ) Notice: Subject to any disclaimer, the term of this patent is extended or adjusted under 35 U.S.C. 154(b) by 690 days.

(21) Appl. No.: 12/504,099

(22) Filed: Jul. 16, 2009

(65) Prior Publication Data

US 2010/0016874 A1 Jan. 21, 2010

Related U.S. Application Data

(60) Provisional application No. 61/082,256, filed on Jul. 21, 2008.

(51) Int. Cl.
*A61B 17/08* (2006.01)
(52) U.S. Cl.
USPC .......................................................... 606/152
(58) Field of Classification Search
USPC ......... 606/151–156, 157, 158, 213, 215, 216, 606/217; 424/422–424; 623/13.15
See application file for complete search history.

(56) References Cited

U.S. PATENT DOCUMENTS

| | | | |
|---|---|---|---|
| 4,721,109 A * | 1/1988 | Healey | 606/156 |
| 5,019,087 A | 5/1991 | Nichols | |
| 5,057,117 A | 10/1991 | Atweh | |
| 5,356,429 A | 10/1994 | Seare | |
| 5,366,478 A | 11/1994 | Brinkerhoff et al. | |
| 5,376,376 A | 12/1994 | Li | |
| 5,480,436 A | 1/1996 | Bakker et al. | |
| 5,508,036 A | 4/1996 | Bakker et al. | |
| 5,512,291 A | 4/1996 | Li | |
| 5,593,441 A | 1/1997 | Lichtenstein et al. | |
| 5,656,605 A | 8/1997 | Hansson et al. | |
| 5,782,847 A | 7/1998 | Plaia et al. | |
| 5,795,584 A | 8/1998 | Totakura et al. | |

(Continued)

FOREIGN PATENT DOCUMENTS

| WO | WO 2004/010854 A2 | 2/2004 |
|---|---|---|
| WO | WO 2006/023444 A2 | 3/2006 |

OTHER PUBLICATIONS

Product Literature entitled "Solutions for Peripheral Nerve Surgery", NeuraWrap™ nerve protector, undated.

(Continued)

*Primary Examiner* — Julian W Woo
(74) *Attorney, Agent, or Firm* — Tarolli, Sundheim, Covell & Tummino LLP

(57) ABSTRACT

An apparatus for connecting two elongate body tissues is described. A flexible outer surface has a first outer end longitudinally spaced from a second outer end. A flexible inner surface has a first inner end longitudinally spaced from a second inner end. A first end aperture is defined by a flexible connection between the first outer end and the first inner end. The first end aperture is configured to accept a first elongate body tissue. A second end aperture is defined by a flexible connection between the second outer end and the second inner end. The second end aperture is configured to accept a second elongate body tissue. The outer and inner surfaces are configured for relative eversion operative to longitudinally shift an instantaneous midpoint of the apparatus with respect to a reference location on the inner surface. A method of using the apparatus is also provided.

20 Claims, 3 Drawing Sheets

(56) References Cited

U.S. PATENT DOCUMENTS

| | | |
|---|---|---|
| 5,997,895 A | 12/1999 | Narotam et al. |
| 6,080,168 A | 6/2000 | Levin et al. |
| 6,270,530 B1 | 8/2001 | Eldgridge et al. |
| 6,302,897 B1 | 10/2001 | Rousseau |
| 6,350,285 B2 | 2/2002 | Gerlach et al. |
| 6,383,201 B1 | 5/2002 | Dong |
| 6,471,714 B1 | 10/2002 | Kim |
| 6,716,225 B2 | 4/2004 | Li et al. |
| 6,719,781 B1 * | 4/2004 | Kim .......................... 623/1.13 |
| 6,736,823 B2 | 5/2004 | Darois et al. |
| 6,736,854 B2 | 5/2004 | Vadurro et al. |
| 6,790,213 B2 | 9/2004 | Cherok et al. |
| 6,964,674 B1 | 11/2005 | Matsuura et al. |
| 7,004,971 B2 | 2/2006 | Serhan et al. |
| 2002/0052622 A1 | 5/2002 | Rousseau |
| 2002/0183767 A1 * | 12/2002 | Adams et al. ................. 606/151 |
| 2005/0261782 A1 | 11/2005 | Hoganson |
| 2005/0283256 A1 | 12/2005 | Sommerich et al. |
| 2005/0288706 A1 * | 12/2005 | Widomski et al. ............ 606/213 |
| 2006/0041320 A1 | 2/2006 | Matsuda |
| 2006/0100647 A1 | 5/2006 | Doi et al. |
| 2007/0100358 A2 | 5/2007 | Romero-Ortega et al. |

OTHER PUBLICATIONS

Product Literature entitled "Advanced Solutions for Peripheral Nerve Repair", *NeuraGen™ nerve guide*, undated.

* cited by examiner

APPARATUS AND METHOD FOR CONNECTING TWO ELONGATE BODY TISSUES

RELATED APPLICATION

This application claims priority from U.S. Provisional Patent Application Ser. No. 61/082,256 filed Jul. 22, 2008, the subject matter of which is hereby incorporated by reference in its entirety.

TECHNICAL FIELD

The present invention relates to an apparatus and method for connecting two elongate body tissues and, more particularly, to a sheath for longitudinally connecting a first elongate body tissue with a second elongate body tissue, and a method for using the sheath.

BACKGROUND OF THE INVENTION

Since the first reported attempt at surgical nerve repair in the thirteenth century, the restoration of normal nerve function following nerve injury has remained a persistently elusive goal. It was believed that damage to nerves resulted in a permanent loss of all function due to the failure of the nerve tissue to regenerate. It was then learned that the regenerative capacities of both the peripheral nervous system and the central nervous system are considerable, if the appropriate conditions are provided.

Many different approaches have been taken in an attempt to regenerate a nerve that has been subjected to trauma, be it a severed nerve or a nerve having a gap between its proximal and distal ends. One such technique, called neurorrhaphy, involves the actual suturing of the proximal and distal ends of the severed nerve. However, scar tissue resulting from the surgical manipulations required for direct proximal-to-distal nerve suture frequently interferes with the growth of proximal stump axons into the distal nerve stump. As a result, prospects for achieving significant reennervation are reduced. The end result may be a lack of full return of motor and/or sensory function.

Microsurgical grafting has been used to span a defect between two nerve stumps. This technique involves surgically grafting a piece of a nerve from another part of the body. This approach, too, has limitations. Suture techniques and/or grafting have not always been sufficient for repair of a severe defect. In many instances, there was either no nerve growth or only growth of connective tissue. Thus, the functional results of surgical repair of peripheral nerve injuries have been disappointing in spite of improved surgical techniques.

Strategies have been devised for attempting to enhance the regeneration of peripheral nerves (those outside the spinal cord and brain). In addition to decalcified bone and vessels, fascia lata, fat, muscle, parchment, Cargile membrane, gelatin, agar, rubber, fibrin film, and various metals have been used to link nerve stumps with varying degrees of success. Many materials failed because they incited a foreign body reaction, produced constricting scar tissue, were technically difficult to apply, or required secondary operation for their removal.

Various enhancements in both entubulation and nerve wrapping have continued in order to facilitate nerve repair. Both biodegradable and non-resorbable materials have been used to act as a sleeve or channel to promote growth and regeneration in severed nerves which have been sutured together or in connection with nerve grafts. However, the results have been less than satisfactory, due at least in part to trauma inflicted upon the severed nerves during engagement with the sleeve or wrap, as the nerves are threaded and pushed into the sleeves.

Tendon repair involves similar structures, considerations, and complications as those discussed above with respect to nerve repair. Additionally, a tendon should be free to move longitudinally within its sheath (the "peritenon") or channel during movement of the affected area. Scar tissue, which occur under similar circumstances to the nerve scar tissue above, inhibits this free gliding of the tendon within the peritenon, thus tethering the tendon in an unwanted manner.

SUMMARY OF THE INVENTION

In an embodiment of the present invention, an apparatus for connecting two elongate body tissues is described. A flexible outer surface has a first outer end longitudinally spaced from a second outer end. A flexible inner surface has a first inner end longitudinally spaced from a second inner end. A first end aperture is defined by a flexible connection between the first outer end and the first inner end. The first end aperture is configured to accept a first elongate body tissue. A second end aperture is defined by a flexible connection between the second outer end and the second inner end. The second end aperture is configured to accept a second elongate body tissue. The outer and inner surfaces are configured for relative eversion operative to longitudinally shift an instantaneous midpoint of the apparatus with respect to a reference location on the inner surface.

In an embodiment of the present invention, a sheath for longitudinally connecting at least one of a first nerve sheath and a first tendon stump with at least one of a second nerve sheath and a second tendon stump is described. A flexible outer surface has a first outer end longitudinally spaced from a second outer end. A flexible inner surface has a first inner end longitudinally spaced from a second inner end. A first end aperture is defined by a flexible connection between the first outer end and the first inner end. The first end aperture is configured to accept at least one of a first nerve stump and a first tendon stump. A second end aperture is defined by a flexible connection between the second outer end and the second inner end. The second end aperture is configured to accept at least one of a second nerve stump and a second tendon stump. The outer and inner surfaces are configured for relative eversion operative to longitudinally shift an instantaneous midpoint of the apparatus with respect to a reference location on the inner surface.

In an embodiment of the present invention, a method for connecting two elongate body tissues is described. A flexible sheath is provided. The flexible sheath includes a flexible outer surface, a flexible inner surface, and first and second end apertures defined by flexible connections between the outer and inner surface. The flexible sheath has a substantially tubular structure. A proximal end of a first elongate body tissue is inserted a desired distance into the first end aperture. An installed length of the first elongate body tissue is engaged with the inner surface of the flexible sheath. The flexible sheath is at least partially everted to longitudinally shift an instantaneous midpoint in a distal direction with respect to the first elongate body tissue. The flexible sheath is held in temporary engagement with an additional length, greater than the installed length, of the first elongate body tissue. A distal end of a second elongate body tissue is inserted a desired distance into the second end aperture while the flexible sheath is in temporary engagement with the additional length of the first elongate body tissue. The flexible sheath is at least partially un-everted to release the additional length of the first elongate body tissue and concurrently engage an installed length of the second elongate body tissue. The flexible sheath longitudinally shifts an instantaneous midpoint in the distal direction to connect the first and second elongate body tissues.

BRIEF DESCRIPTION OF THE DRAWINGS

For a better understanding of the invention, reference may be made to the accompanying drawings, in which.

DESCRIPTION OF EMBODIMENTS

Figure 1:
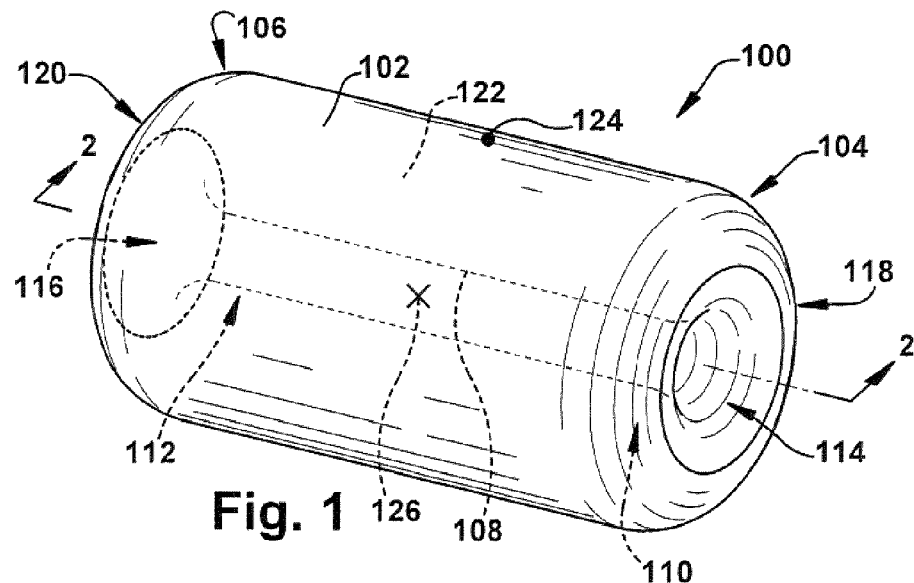
FIG. 1 is a perspective side view of one embodiment of the present invention.

In accordance with the present invention, FIG. 1 depicts a substantially tubular apparatus 100 for connecting two elongate body tissues. For example, the apparatus 100 could be a flexible sheath for longitudinally connecting at least one of a first nerve stump and a first tendon stump with at least one of a second nerve stump and a second tendon stump. For ease of description, the elongate body tissues will be described herein as first and second nerve stumps. However, the present invention is not limited in application by this description.

A flexible outer surface 102 has a first outer end 104 longitudinally spaced from a second outer end 106. A flexible inner surface 108 has a first inner end 110 longitudinally spaced from a second inner end 112. At least one of the outer and inner surfaces 102 and 108 may be cylindrical, substantially as shown in FIG. 1. The outer and inner surfaces 102 and 108, like all structures of the apparatus 100, may be made of any suitable material and in any desired manner. For example, at least a portion of the apparatus 100 may be made of a vinyl, synthetic collagen or biologic material, polylactic acid-based material, or any other type of membrane, which may be folded over onto itself and sealed to define a double-walled toroidal structure. Any of the structures of the apparatus may be made from multiple layers of membranes, films, meshes, or the like, of any suitable material(s).

Similarly, the apparatus 100 may be at least partially made of a frictionally enhanced material, such as one having an embossed texture and/or a rubberized coating, in order to more firmly grasp the first and second nerve stumps in particular applications of the present invention. At least a portion of the apparatus 100 may include a drug-eluting material and/or feature. "Elute" is used herein to indicate that a therapeutic agent is released, leached, diffused, or otherwise provided to the target tissue. Therefore, at least a portion of the apparatus 100 could be adapted to elute a therapeutic agent, such as, but not limited to, an anesthetic, anti-inflammatory, or antiseptic fluid, to the first and/or second nerve stumps, or to any nearby body tissue. It is also contemplated that at least a portion of the apparatus could be made of a biodegradable material, to deteriorate/dissolve, or otherwise become incorporated within the body after a predetermined period of time during which the first and second nerve stumps are likely to have grown together.

The apparatus 100 may have any suitable size, shape, proportions, or other physical characteristics as desired for a particular application of the present invention. For example, the apparatus 100 shown in the Figures may be in the range of approximately 1 millimeter to 10 millimeters in diameter and in the range of approximately 7 millimeters to 60 millimeters long. The actual dimensions may be readily chosen by one of ordinary skill in the art, and may at least partially depend upon whether the apparatus 100 is used with a nerve, tendon, or another body tissue application.

A first end aperture 114 is defined by a flexible connection between the first outer end 104 and the first inner end 110. The first end aperture 114 is configured to accept a first nerve stump, as described below. A second end aperture 116 is defined by a flexible connection between the second outer end 106 and the second inner end 112. The second end aperture 116 is configured to accept a second nerve stump, as described below.

The first end aperture 114 may be at least partially defined by a flexible first endwall 118 interposed between the first outer end 104 and the first inner end 110. The second end aperture 116 may be at least partially defined by a flexible second endwall 120 interposed between the second outer end 106 and the second inner end 112. The first and second endwalls 118 and 120, when present, may be of any suitable material and/or configuration. For example, the first and second endwalls 118 and 120 may be substantially planar and thus result in a right cylindrical configuration (not shown) of the apparatus 100. Though the first and second endwalls 118 and 120 (among other structures) are described herein as being "flexible", the actual degree of flexibility of all structures of the apparatus 100 may be chosen to provide desired characteristics to the apparatus 100 and does not need to match the flexibility of other structures of the apparatus. Therefore, the first and/or second endwalls 118 and 120 may be substantially rigid in some applications of the present invention. When the first and/or second endwalls 118 and 120 are omitted from the apparatus 100, the inner and outer end connections described previously will serve to define the first and second end apertures 114 and 116.

One of ordinary skill in the art will recognize, particularly in light of the below discussion on the use of the apparatus 100, that the described features and structures of the apparatus may not be clearly delineated and/or defined at all times during operation of the apparatus, at least because of the limits of language in describing certain structures of the apparatus. For example, as the apparatus 100 is used in the envisioned manner, the outer surface 102 may be temporarily located at least partially "inside" the apparatus, while the inner surface 108 may be temporarily located at least partially "outside" the apparatus. However, these transient locations (which may be different from the resting positions of the named elements) and the descriptions of the elements do not limit the present invention. As another example, at least a portion of the apparatus 100 may be integrally formed, and thus the boundaries of the various surfaces may be somewhat arbitrarily determined, based upon the steady-state locations thereof.

In other words, the descriptors used for various features of the apparatus 100 may be considered to define those elements with the apparatus shown in the steady-state, balanced condition of FIG. 1, wherein the apparatus is not under any unbalancing forces (as will be described shortly), which may cause relative shifting of the named and depicted structures. Optionally, the apparatus 100 may be configured to return to the FIG. 1 resting state when any forces acting thereupon are released. Alternatively, there may be at least one other steady-state position (not shown) in which the apparatus 100 is at rest, but the named structures are not in the positions depicted in FIG. 1. One of ordinary skill in the art can readily discern the features and operation of the present invention by reference to the instant Figures and description, regardless of the nomenclature, structure, and/or instantaneous position of any structures of a particular embodiment of the present invention.

There may be a closed intermediate space 122 between the outer and inner surfaces 102 and 108, which acts to laterally space the outer and inner surfaces. When present, the intermediate space 122 may containing a cushioning medium (not shown) such as, but not limited to, a suitable saline or other nontoxic solution or fluid having a desired viscosity and other properties. For example, a cushioning medium such as a hyaluronic acid-based fluid might be chosen if the apparatus 100 is resorbable or otherwise biodegradable. Alternately, the outer and inner surfaces may be in direct contact with each other inside the apparatus 100, in lieu of an intermediate space 122.

The outer and inner surfaces 102 and 108 are each configured for relative eversion operative to longitudinally shift an instantaneous midpoint 124 of the apparatus 100 with respect to a reference location 126 on the inner surface 108. A chosen one of the instantaneous midpoint 124 and the reference location 126 may be substantially stationary relative to an external standard location (not shown). The term "evert" is used herein to indicate a shifting of the "everting" structure(s) away from the steady-state position in a longitudinal direction (toward the left or right, as the Figures are oriented), due to the influence of an exerted outside force. An everted structure can be "un-everted", or relaxed, back into the steady-state position, and may be designed to do so automatically upon release of the outside force.

The instantaneous midpoint 124 and the reference location 126 may not be actually present on the apparatus 100, but are shown in the Figures to assist with description of the present invention. The instantaneous midpoint 124 and the reference location 126 may have any desired placements, configurations, and properties, and are merely included herein to facilitate description of the operation of the apparatus 100. The placement of the instantaneous midpoint 124 and the reference location 126 in the Figures is arbitrarily chosen and bears no significance. It should be noted that the instantaneous midpoint 124 (shown as a dot) of the apparatus 100 shifts with respect to the outer surface 102 as the outer and inner surfaces 102 and 108 relatively evert, but that the reference location 126 (shown as an "X") stays in its designated relationship to the inner surface 108, in the below description. Therefore, the apparatus 100 is operative to produce relative motion between the instantaneous midpoint 124 and the reference location 126.

Figure 2:
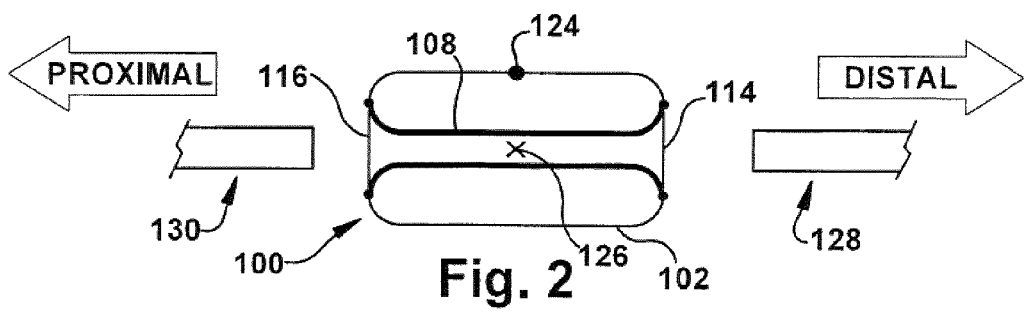
FIGS. 2-9 are cross-sectional views taken along line 2-2 of FIG. 1 and depicting an example sequence of operation of an embodiment of the present invention.

The sequence of operation of an embodiment of the present invention is shown in FIGS. 2-9. Though the inner surface 108 is shown with a thicker line than the outer surface 102, for clarity of depiction, the outer and inner surfaces may have any desirable relative weights or thicknesses. In FIGS. 2-9, the distal direction is toward the right side of the drawings, as oriented on the page, and the proximal direction is toward the left side, as shown in FIG. 2 by the labeled arrows. The proximal and distal directions are longitudinally oriented, as shown.

In FIG. 2, the apparatus 100 is shown at rest in a steady state position, with a first elongate body tissue (here a first nerve stump 128) located distally from the apparatus, and a second elongate body tissue (here a second nerve stump 130) located proximally from the apparatus. The instantaneous midpoint 124 and reference location 126 are aligned in an initial position. In FIG. 2, the apparatus 100 has been placed into a desired location within the patient's body, with already-prepared first and second nerve stumps 128 and 130 in appropriate proximity for the joining or connection procedure, as discussed below.

Figure 3:
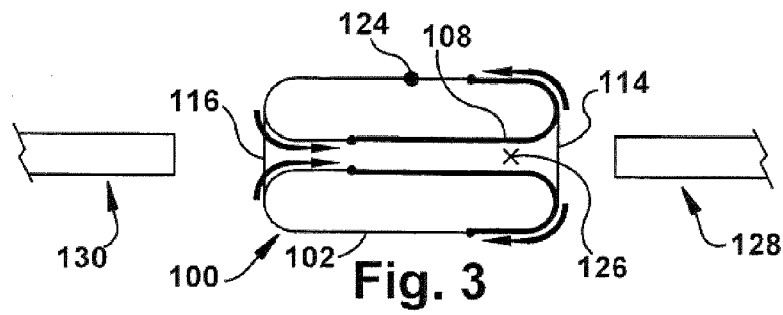

FIG. 3 depicts an optional preparatory step to using the apparatus 100. One of ordinary skill in the art can readily provide an apparatus (not shown) in which the step of FIG. 3 is extraneous. However, the apparatus 100 depicted in the sequence of FIGS. 2-9 includes a "shape memory" configuration that urges the apparatus back to the resting position of FIG. 2 unless a force to the contrary is exerted upon the apparatus. Therefore, in FIG. 3, the apparatus 100 is prepared for engagement with the first nerve stump 128 by being partially everted in a rolling or "tank tread" manner, as shown by the arrows indicating the movement of the outer and inner surfaces 102 and 108. That is, the apparatus 100 is at least partially everted to longitudinally shift the reference location 126 of the apparatus in a distal direction with respect to the first nerve stump 128 before the first nerve stump is engaged with the apparatus. This eversion is caused by an outside force (not shown) exerted on the apparatus 100, and the outside force is maintained to hold the apparatus in the position shown in FIGS. 3 and 4.

Figure 4:
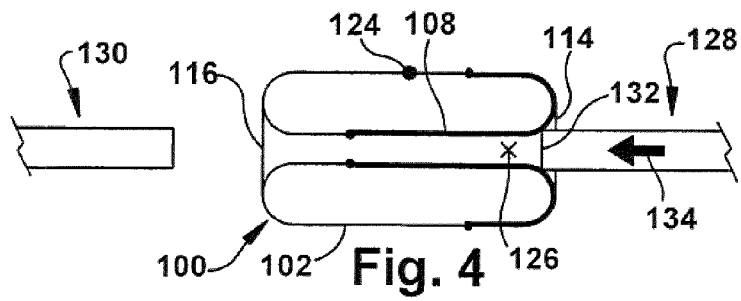

Regardless of whether the apparatus 100 has undergone the preparatory step of FIG. 3, a proximal end 132 of the first nerve stump 128 may be moved proximally and inserted a desired distance into the first end aperture 114, as shown in FIG. 4 by the proximal insertion arrow 134. The phrase "inserted into" is used herein to indicate any amount of insertion sufficient to allow the inner surface 108 to engage the first or second nerve stump 128 or 130, as the case may be, in the desired manner. It is not necessary that a substantial insertion be performed. It is contemplated that when the first or second nerve stump 128 or 130 crosses the plane of the first or second end aperture 114 or 116, respectively, a sufficient amount to be grasped and engaged by the apparatus 100. However, different amounts of insertion, including those in which the first or second nerve stump 128 or 130 does not cross the plane of the first or second end aperture 114 or 116, may be sufficient in a particular embodiment of the present invention.

While the connection between the outer and inner surfaces 102 and 108 has wrapped around to the outside of the apparatus 100, as shown in FIGS. 3 and 4, the first and second end apertures 114 and 116 are shown as still being in substantially the same positions as in the steady-state configuration of FIG. 2. This adjustment of the first and second end aperture 114 and 116 locations relative to other structures of the apparatus 100 in the present description is done to emphasize the function of the apparatus while maintaining logical element names and labeling and does not limit the properties or function of any structure of the apparatus.

Figure 5:
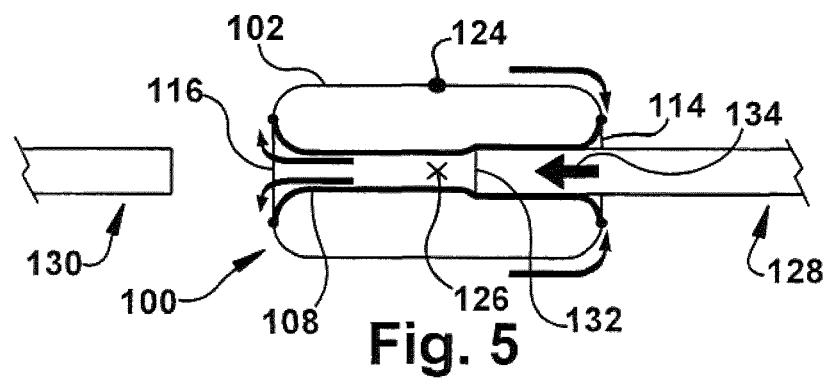

In FIG. 5, the outside force has been released, a different outside force (not shown) has optionally been applied to the apparatus 100, and the apparatus has un-everted and rolled back to its steady-state position with the first nerve stump 128 held by the inner surface 108. As the apparatus 100 un-everts, the proximal end 132 of the first nerve stump 128 is drawn into the interior of the apparatus until an installed length of the first nerve stump is engaged with the inner surface 108 of the apparatus at rest, as shown in FIG. 5. In the remaining steps of the sequence, shown in FIGS. 5-9, the proximal end 132 of the first nerve stump 128 will remain relatively stationary with respect to the reference location 126. However, different lengths of the first nerve stump 128 may come into engagement with the apparatus 100 at different stages (such as those shown in FIGS. 2-9) during mutual connection of the first and second nerve stumps 128 and 130 via the apparatus. As evidenced by the return of the instantaneous midpoint 124 and the reference location 126 to their initial (FIG. 2) spatial relationship, the apparatus 100 has returned to the steady-state, resting position in FIG. 5.

One of ordinary skill in the art could place the first nerve stump 128 into the FIG. 5 engagement with the apparatus 100 in a manner other than that shown in FIGS. 2-5. For example, the proximal end 132 of the first nerve stump 128 could be threaded or otherwise placed into the first end aperture 114 without substantial eversion of the apparatus 100. If the first nerve stump 128 (or another type of first elongate body tissue used with the present invention) is artificially created, the apparatus 100 could be manufactured in conjunction with the first nerve stump 128 and provided to the patient already in the FIG. 5 configuration with the first nerve stump.

Figure 6:
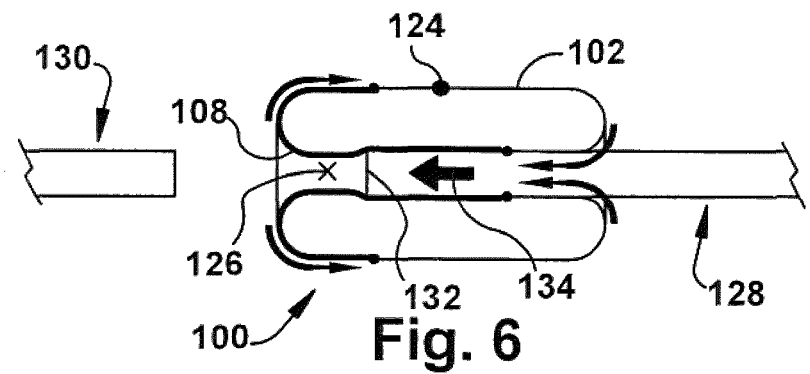

Proceeding to FIG. 6, the apparatus 100 is being at least partially everted to longitudinally shift the reference location 126 of the apparatus 100 in a proximal direction. Thus, an additional length of the first nerve stump 128, greater than the installed length associated with a resting state apparatus 100, is held in temporary engagement with the apparatus. As with the sequence of operation of FIGS. 3-4, the sequence of operation of FIGS. 6-7 can be produced through the application and/or maintenance of an outside force (not shown) upon the apparatus 100.

Figure 7:
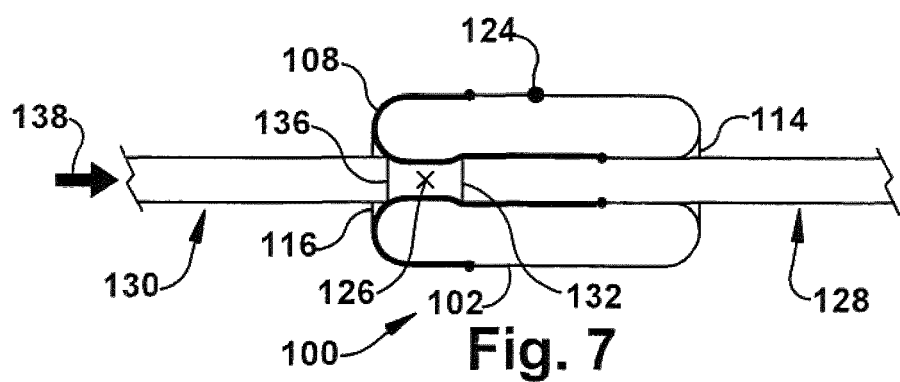

Once the apparatus 100 has been placed into the configuration of FIG. 6, the second nerve stump 130 is associated with the apparatus as shown in FIG. 7. That is, a distal end 136 of the second nerve stump 130 is inserted a desired distance into the second end aperture 116, in the direction of the distal insertion arrow 138, while the apparatus 100 is in temporary engagement with the additional length of the first nerve stump 128. At this step, the proximal end 132 of the first nerve stump 128 and the distal end 136 of the second nerve stump 130 have substantially attained their final relative positions with respect to the reference location 126.

Figure 8:
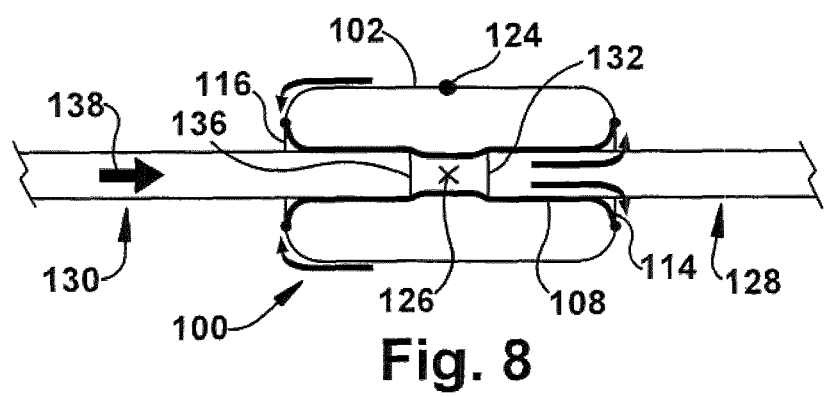

The sequence then proceeds from FIG. 7 to FIG. 8, wherein the apparatus 100 has been at least partially un-everted (as before, through the release of the outside force or application of a different outside force) to release the additional length of the first nerve stump 128 and concurrently engage an installed length of the second nerve stump 130. During this un-eversion, the apparatus 100 shifts the instantaneous midpoint 124 in a distal direction, substantially into its original relationship with the reference location 126, to connect the first and second nerve stumps 128 and 130 in a desired manner.

Figure 9:
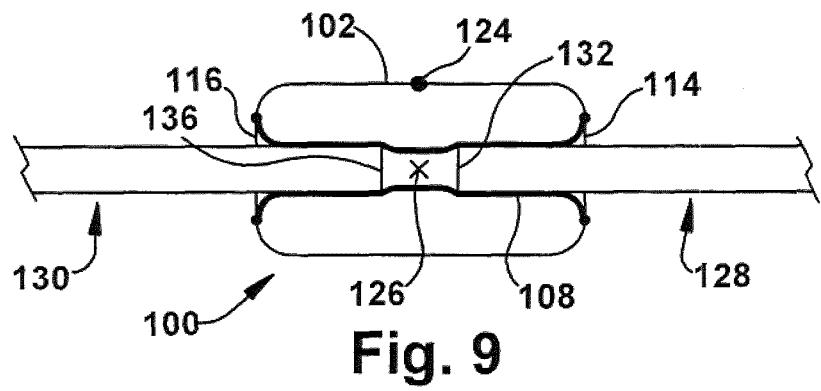

At this point, the apparatus 100 has re-attained its resting or steady-state configuration, similar to that of FIG. 2, but with the first and second nerve stumps 128 and 130 held therein, as shown in FIG. 9, for mutual connection. By arranging for the apparatus 100 to be in a steady-state condition when the first and second nerve stumps 128 and 130 are connected, unbalanced forces and stresses within, and acting on, the apparatus and first/second nerve stumps may be avoided.

In the FIG. 9 configuration, the apparatus 100 and connected first and second nerve stumps 128 and 130 may be placed within the patient's body as desired, optionally with the assistance of one or more anchor features (not shown) on the apparatus. Compressive force may be exerted in a radial orientation on the first and second nerve stumps 128 and 130, and/or frictional force may be exerted in a longitudinal orientation on the first and second nerve stumps, when the first and second nerve stumps are connected by the apparatus 100 in the manner shown and described herein. Therefore, the first and second nerve stumps can be placed gently and nontraumatically into a desired connected arrangement and left within the body in that desired linked configuration. The apparatus 100 thus facilitates regeneration and/or healing of the first and second nerve stumps 128 and 130 within the body. Optionally, and as previously mentioned, the apparatus 100 may be biodegradable and disintegrate within the body after a predetermined period of time, leaving the first and second nerve stumps 128 and 130 united by new growth (not shown) enabled by the apparatus. Additionally, and particularly when used with tendon stumps (not shown), the apparatus 100 may be dimensioned to allow relative movement between the (repaired) tendon and a corresponding peritenon or other channel, optionally through at least partial eversion of the apparatus 100, even if scar tissue has formed at or near the installation site.

While aspects of the present invention have been particularly shown and described with reference to the preferred embodiment above, it will be understood by those of ordinary skill in the art that various additional embodiments may be contemplated without departing from the spirit and scope of the present invention. For example, each of the outer and inner surfaces 102 and 108 could have any suitable shape (cross-sectional in any plane or as seen in any other view), such as, but not limited to, an hourglass or other center-pinched shape, a cone or other tapered shape, a diamond or other center-expanded shape, or the like. Any portion of the apparatus 100 may be adapted to place the first and second nerve stumps 128 and 130, or other elongate body tissues used with the apparatus, into either an electrically conductive or insulative relationship, or into any desired chemical relationship. The first and second nerve stumps 128 and 130 could be placed into longitudinal, end-to-end contact or even be overlapped within the apparatus 100, rather than being slightly separated as depicted in FIGS. 2-9. The apparatus 100 may be assembled from multiple components or integrally formed. The "proximal" and "distal" directional indications and movements described herein are solely imposed for ease of description and do not limit the positioning or functioning of the apparatus 100. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for connecting two elongate body tissues, the apparatus comprising:
    a flexible outer surface having a first outer end longitudinally spaced from a second outer end;
    a flexible, smooth inner surface having a first inner end longitudinally spaced from a second inner end;
    a first end aperture defined by a flexible connection between the first outer end and the first inner end, the first end aperture being configured to accept a first elongate body tissue; and
    a second end aperture defined by a flexible connection between the second outer end and the second inner end, the second end aperture being configured to accept a second elongate body tissue;
    wherein the outer and inner surfaces are configured for relative eversion operative to longitudinally shift an instantaneous midpoint of the apparatus with respect to a reference location on the inner surface upon longitudinal movement of the apparatus along the first and second elongate body tissues.

2. The apparatus of claim 1, wherein at least one of the outer and inner surfaces is cylindrical.

3. The apparatus of claim 1, including a closed intermediate space between the outer and inner surfaces, and the intermediate space contains a cushioning medium.

4. The apparatus of claim 3, wherein the cushioning medium comprises one of saline and hyaluronic-based solution.

5. The apparatus of claim 3, wherein the intermediate space is sealed to prevent the cushioning medium from exiting the intermediate space.

6. The apparatus of claim 1, wherein the first end aperture is at least partially defined by a flexible first endwall interposed between the first outer end and the first inner end, and the second end aperture is at least partially defined by a flexible second endwall interposed between the second outer end and the second inner end.

7. The apparatus of claim 1, being at least partially formed of a frictionally enhanced material.

8. The apparatus of claim 1, wherein at least one of the first and second elongate body tissues is at least one of a nerve and a tendon.

9. The apparatus of claim 1, wherein the inner and outer surfaces are at least partially formed of a drug-eluting material.

10. The apparatus of claim 1, wherein a leading edge of the first elongate body tissue is accepted by the first end aperture, the smooth inner surface and the first elongate body tissue having a continuous interface from the leading edge of the first elongate body tissue to the first end aperture.

11. A sheath for longitudinally connecting at least one of a first nerve stump and a first tendon stump with at least one of a second nerve stump and a second tendon stump, the sheath comprising:
a flexible outer surface having a first outer end longitudinally spaced from a second outer end;
a flexible, smooth inner surface having a first inner end longitudinally spaced from a second inner end;
a closed intermediate space between the outer and inner surfaces containing a cushioning medium;
a first end aperture defined by a flexible connection between the first outer end and the first inner end, the first end aperture being configured to accept at least one of a first nerve stump and a first tendon stump; and
a second end aperture defined by a flexible connection between the second outer end and the second inner end, the second end aperture being configured to accept at least one of a second nerve stump and a second tendon stump;
wherein the outer and inner surfaces are configured for relative eversion operative to longitudinally shift an instantaneous midpoint of the sheath with respect to a reference location on the inner surface upon longitudinal movement of the apparatus along the at least one of the first nerve stump and the first tendon stump and the at least one of the second nerve stump and the second tendon stump.

12. The sheath of claim 11, wherein at least one of the outer and inner surfaces is cylindrical.

13. The sheath of claim 11, wherein the first end aperture is at least partially defined by a flexible first endwall interposed between the first outer end and the first inner end, and the second end aperture is at least partially defined by a flexible second endwall interposed between the second outer end and the second inner end.

14. The sheath of claim 11, being at least partially formed of a frictionally enhanced material.

15. The sheath of claim 11, being at least partially formed of a drug-eluting material.

16. The sheath of claim 11, wherein the cushioning medium comprises one of saline and a hyaluronic-based solution.

17. The sheath of claim 11, wherein the intermediate space is sealed to prevent the cushioning medium from exiting the intermediate space.

18. The sheath of claim 11, wherein the inner and outer surfaces are at least partially formed of a drug-eluting material.

19. The sheath of claim 11, wherein a leading edge of the first elongate body tissue is accepted by the first end aperture, the inner surface and the first elongate body tissue having a continuous interface from the leading edge of the first elongate body tissue to the first end aperture.

20. The sheath of claim 11, wherein the smooth inner surface has a tubular shape.

* * * * *